US007041480B2

(12) United States Patent
Abarzúa

(10) Patent No.: US 7,041,480 B2
(45) Date of Patent: *May 9, 2006

(54) GENERATION OF SINGLE-STRAND CIRCULAR DNA FROM LINEAR SELF-ANNEALING SEGMENTS

(75) Inventor: Patricio Abarzúa, West Caldwell, NJ (US)

(73) Assignee: Qiagen GmbH, Hilden (DE)

( * ) Notice: Subject to any disclaimer, the term of this patent is extended or adjusted under 35 U.S.C. 154(b) by 478 days.

This patent is subject to a terminal disclaimer.

(21) Appl. No.: 10/196,539

(22) Filed: Jul. 16, 2002

(65) Prior Publication Data

US 2003/0108902 A1 Jun. 12, 2003

Related U.S. Application Data

(63) Continuation of application No. 09/723,685, filed on Nov. 28, 2000, now Pat. No. 6,498,023.

(60) Provisional application No. 60/168,511, filed on Dec. 2, 1999.

(51) Int. Cl.
*C12P 19/34* (2006.01)
(52) U.S. Cl. .................................. 435/91.2
(58) Field of Classification Search .................. 435/6, 435/91.2, 91.1
See application file for complete search history.

(56) References Cited

U.S. PATENT DOCUMENTS

| 5,516,663 A | * | 5/1996 | Backman et al. ........... 435/91.2 |
| 5,683,985 A | | 11/1997 | Chu et al. |
| 5,728,526 A | * | 3/1998 | George et al. ................. 435/6 |
| 5,945,312 A | | 8/1999 | Goodman et al. |
| 6,235,502 B1 | * | 5/2001 | Weissman et al. ......... 435/91.1 |

FOREIGN PATENT DOCUMENTS

| WO | WO/9201813 | 2/1992 |
| WO | WO98/02449 | 1/1998 |

OTHER PUBLICATIONS

Wemmer et al. Preparation and melting of single strand circular DNA loops. 1985. Nucleic Acids Research vol. 13(23) 8611-8621.*
Betz et al., "Variants of a Cloned Synthetic Lactose Operator", Gene, 13:1-12 (1981).

(Continued)

*Primary Examiner*—Kenneth R. Horlick
*Assistant Examiner*—Heather G. Calamita
(74) *Attorney, Agent, or Firm*—Needle & Rosenberg

(57) ABSTRACT

The present invention provides a method for the rapid simultaneous production of a plurality of single-stranded DNA circles having a predetermined size and nucleotide sequence using pre-designed hairpin oligonucleotides containing complementary sequences for directing ligation to form dumbbell-shaped monomers followed by heat denaturation to yield single-stranded DNA circles.

20 Claims, 4 Drawing Sheets

OTHER PUBLICATIONS

Wemmer et al., "Preparation and Melting of Single Strand Circular DNA Loops", Nucleic Acids Research, vol. 13, No. 23 (1985).

Diegelman et al., "Generation of Circular RNAs and Trans-cleaving Catalytic RNAs by Rolling Transcription of Circular DNA Oligonucleotides Encoding Hairpin Ribozymes", Nucleic Acids Research, vol. 26, No. 13, pp. 3235-3241 (1998).

Lim et al., "Synthesis of DNA Dumbbells: Chemical vs. Enzymatic Ligation of Self-Complementary Oligonucleotides", Nucleoside and Nucleotides, 16 (1&2), pp. 41-51 (1997).

Erie et al., "A Dumbbell-Shaped, Double-Hairpin Structure of DNA: A Thermodynamic Investigation", Biochemistry, pp. 7150-7159 (1987).

Naritsin et al., "Melting of Oligodeoxynucleotides with Various Structures", pp. 813-825, Journal of Biomolecular Structure & Dynamics. vol. 8, Issue No. 4 (1991).

* cited by examiner

SEQUENCE LISTING

```
<160> NUMBER OF SEQ ID NOS: 6

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Artificial
      hairpin oligonucleotide

<400> SEQUENCE: 1
tgagctgtaa cttgtctcgt attaaactaa agctgagatc tcacgtaca                49

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Artificial
      hairpin oligonucleotide

<400> SEQUENCE: 2
actcaatata gttcttggag aaggtggaat cacactgagt tgtac                    45

<210> SEQ ID NO 3
<211> LENGTH: 5
<212> TYPE: DNA
<213> ORGANISM: Artificial Sequence
<220> FEATURE:
<223> OTHER INFORMATION: Description of Artificial Sequence: "Sticky end"
      complementary sequence of hairpin oligonucleotide

<400> SEQUENCE: 3 tgtac                                                                 5

<210> SEQ ID NO 4
<211> LENGTH: 5
<212> TYPE: DNA
```

```
<213> ORGANISM: Artificial Sequence
<220> FEATURE:
<223> OTHER INFORMATION: Description of Artificial Sequence: "Sticky end"
      complementary sequence of hairpin oligonucleotide

<400> SEQUENCE: 4 gtaca                                                                    5

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence: Hairpin loop
      sequence

<400> SEQUENCE: 5 catga                                                                    5

<210> SEQ ID NO 6
<211> LENGTH: 5
<212> TYPE: DNA
<213> ORGANISM: Artificial Sequence
<220> FEATURE:
<223> OTHER INFORMATION: Description of Artificial Sequence: Hairpin loop
      sequence

<400> SEQUENCE: 6 tcatg                                                                    5
```

GENERATION OF SINGLE-STRAND CIRCULAR DNA FROM LINEAR SELF-ANNEALING SEGMENTS

This application is a continuation of U.S. application Ser. No. 09/723,685 filed 28 Nov. 2000 now U.S. Pat. No. 6,498,023, which claims the priority of U.S. Provisional Application Ser. No. 60/168,511, filed 2 Dec. 1999, the disclosures of which are hereby incorporated by reference in their entirety.

FIELD OF THE INVENTION

The present invention relates to a process for forming single-stranded circular DNA from single-stranded hairpin segments containing complementary sequences directing spontaneous circularization of said segments with subsequent ligation to form single circles.

BACKGROUND OF THE INVENTION

Over the past several decades, research into molecular biology has been greatly enhanced by the plethora of new methodologies made available to workers in the field. Such methods have essentially helped to create the newer area of biotechnology and facilitated its emergence onto the commercial playing field. Especially advantageous has been the methods developed for replicating and amplifying short segments of specific DNA sequences so as to facilitate both the preparation of such sequences as well as amplification for the purpose of identifying desired sequences of DNA within a larger sample.

Most important in this regard has been the development of the polymerase chain reaction (PCR) as a means of exponentially amplifying desired segments of DNA using short primers that flank larger segments whose precise nucleotide sequence is not required to be known. Despite the enormous advantages conferred by such technology, there are certain drawbacks. These include the fact that PCR generates linear duplex sequences of DNA which require denaturation to be converted into single strand as well as further processing if circles are desired. In addition, the various steps of heating and cooling and the different enzymes required for the process make it expensive, time consuming and cumbersome. To respond to these problems, other methodologies have been devised, many of which are essentially modifications of the basic PCR process.

However, PCR remains inadequate for the rapid and inexpensive production of single-stranded circular DNAs. Such DNAs have found use as probes for various so-called target sequences existing within larger segments of single-stranded DNA. Often, such circles have been synthesized with discrete probe segments complementary to the sequences of the target DNA. In such cases, the circle is first synthesized as a so-called "open circle" and permitted to anneal to complementary sequences on a target single-stranded DNA. Once hybridized, the open circle is ligated to form a so-called padlock that is then used as a means of detecting the target DNA. [See: Nilsson et al., Padlock Probes: Circularizing Oligonucleotides for Localized DNA Detection, *Science*, 265, 2085–2088 (1994)]

Single-stranded circular DNA has been found useful in many different areas of biotechnology, both of an experimental as well as commercial nature. One important such use is as a substrate for rolling circle DNA replication. In this procedure, a single-stranded circle of DNA is mixed with a short strand of single-stranded complementary primer DNA and the two separate strands are allowed to anneal. After addition of a DNA polymerase, such as the Klenow fragment, the intact circle is used as a template by the enzyme and then replicated from the 3'-end of the primer strand. After the enzyme has gone around the circular template, it encounters the 5'-end of the primer, which is then displaced from the template strand so that the enzyme continues to move around the circular template while a long, unbroken single strand of DNA is generated. Such single strand has been referred to as single-stranded concatenated DNA (Ruth and Driver, WO 92/01813). The single-stranded circular products of the present invention are ideally suited for use as a substrate in such processes. The product prepared by the method according to the present invention can ultimately yield single-strand concatenated DNA having numerous different sequential segments that can act as probes, detection sites or restriction sites for further processing.

Heretofore, the products of so-called "rolling circle amplification," or RCA, have been used as binding sequences for probes containing complementary sequences for specific sequences located in target DNA whose presence it was desired to detect. In essence, the result is to amplify sequences contained in the circular template to facilitate detection of sequences contained in a target.

In addition, RCA has been used (see Ruth and Driver, WO 92/01813) to produce concatenated single-stranded DNA containing repeated sequences complementary to those contained in the single-stranded circular substrates but containing restriction sites. Thus, when the concatenated DNA is treated with restriction enzymes, it is cut into short, repetitive segments which can, if desired, be ligated to form structures complementary to the original circles. With the addition of primers and DNA polymerase, such process can be repeated to form copies of the original circles. The present invention eliminates the need for such multistep processes by duplicating the desired circles at the outset, thus eliminating the need for a second round of RCA.

Another useful aspect of RCA technology has been to generate circles of different size, combine them, and use these as probes for target DNAs having different target sequences. This has been done either by generating circles of different size and mixing them, or else by running multiple RCA reactions simultaneously in the same reaction mixture, with the relative amounts of starting material determining the relative amounts of products. However, one must first generate the different sized circles to use as substrates.

The methods according to the present invention eliminate the need for such cumbersome processes by providing an easy and effective means of generating circles of any desired sizes and sequences. Thus, using the methods disclosed herein, it is a simple matter to generate circles all of which have the same size, but whose nucleotide sequences are different, or to generate circles of different size and sequence, or any other conceivable combination, all at the same time. The same DNA polymerase will replicate all of the sequences together and their relative abundance in the product will be a function of their relative abundance in the starting mixture.

One of the problems of current RCA technology is that most starting circles are synthesized chemically (to facilitate predetermination of the nucleotide sequence or sequences contained within the circles). Such synthesis has made production of circles larger than about 100 bases both costly and time consuming. Of course, circles larger than about 200 nucleotides cannot be effectively prepared using current technology. Conversely, plasmid technology has not been of much use in this area because the needed starting circles must be single-stranded whereas plasmids are normally duplex DNAs.

Once stretches of single-stranded DNA have been synthesized, the circles are formed enzymatically through the use of ligase enzymes and employing a short guide oligonucleotide. Any remaining unreacted linear oligonucleotide and guide oligonucleotide are then digested with exonucleases. The entire process involves several steps, all of which work with varying efficiencies. The yield of circles by such processes is commonly less than 50% and other, undesired, forms are always present. A simpler and more efficient process for generating such circles is therefore desirable.

BRIEF SUMMARY OF THE INVENTION

The methods according to the present invention involve a different approach from those described hereinabove. In accordance with the present invention, separate segments of single-stranded DNA, each possessing a first short sequence complementary to a second short sequence within the same oligonucleotide, are allowed to self-anneal, thereby forming a pseudo-circular, or hairpin, oligonucleotide having an overhang composed of a portion of a terminal sequence of said single-stranded DNA.

It is a further object of the present invention to provide separate pseudocircular (i.e., hairpin) single stranded DNA structures that can readily be ligated to each other to form, after heat denaturation, enlarged single-stranded circular DNAs containing predetermined nucleotide sequences formed from the sequences of the starting segments.

It is another object of the present invention to provide a method of synthesizing single-stranded circular DNA molecules of varying sizes and sequences using pseudocircular DNA segments as a starting material and without the need for multiple cycles of synthesis and ligation.

It is also an object of the present invention to produce single-stranded circular DNA having predetermined sequences that can be readily replicated without the need for any linear intermediates.

It is likewise an object of the present invention to provide a means of producing multiple copies of single-stranded DNA circles of varying sizes and of any desired sequences for subsequent mixing to yield a single reaction mixture for further rolling circle replication.

It is another object of the present invention to provide a means of synthesizing single-stranded DNA circles capable of ready use in subsequent processes, such as rolling circle amplification.

It is a still further object of the present invention to provide hairpin oligonucleotides with complementary ends (i.e., complementary overhang regions) that comprise restriction sites for endonucleases to provide, after appropriate ligating and denaturation, single stranded circles whose RCA products can be cut by the same restriction enzyme to regenerate hairpin oligonucleotides, thereby providing, inter alia, an enzymatic source of oligonucleotides for production of circles without the need of chemical synthesis.

It is also an object of the present invention to provide hairpin oligonucleotides with coherent ends for ligation to DNA restriction fragments of any desired size and sequence to form circles for amplification by RCA.

DETAILED DESCRIPTION OF THE INVENTION

Figure 1:
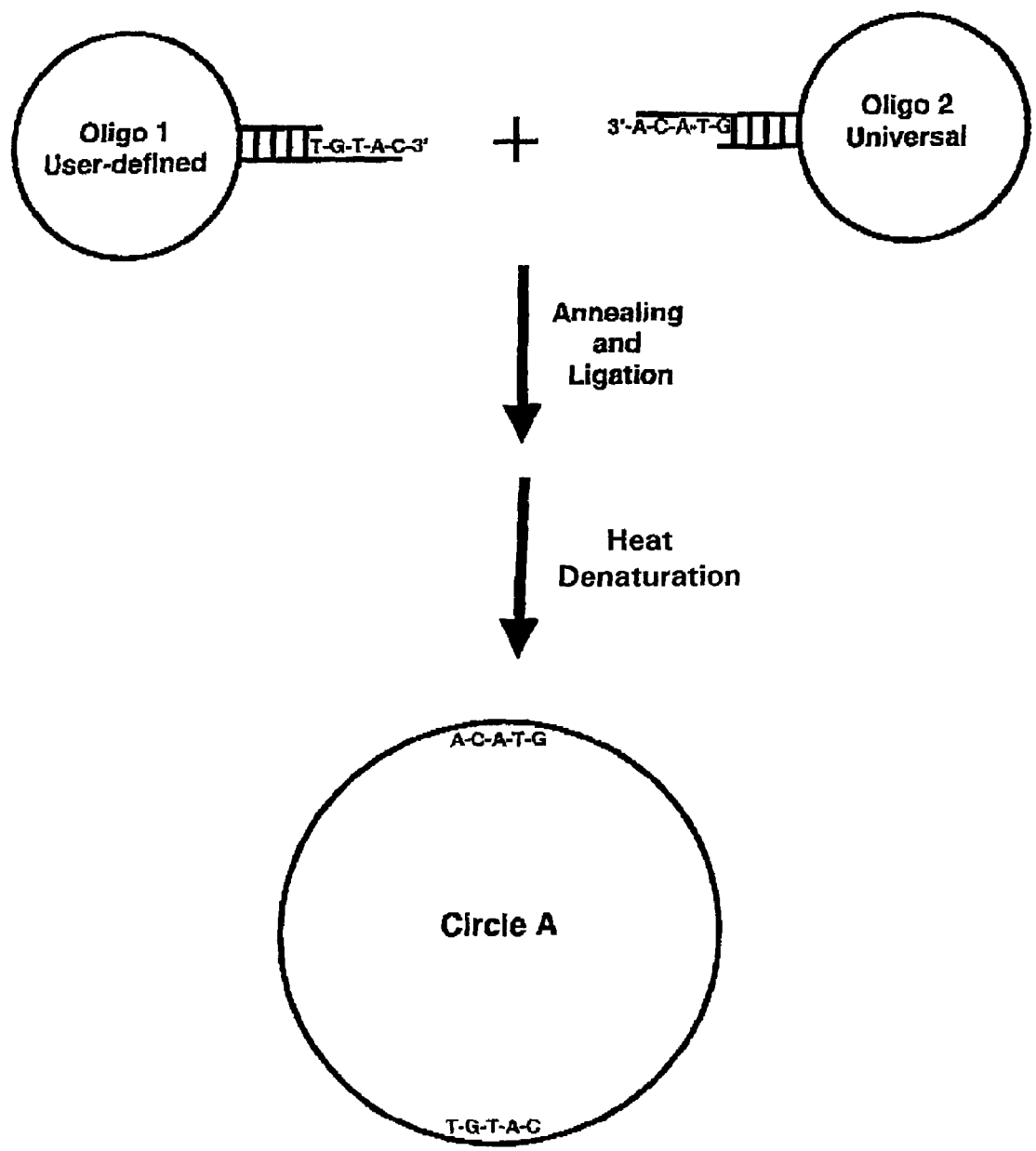
FIG. 1 shows a schematic diagram of the overall process according to the present invention for the simple and rapid production of single stranded DNA circles. Here, two hairpin oligonucleotides, each circularized by internal complementary sequences, are permitted to anneal to each other via complementary overhangs, or coherent tail sequences (here, each with an overhang containing a pentanucleotide complementary 5'-TGTAC-3' (SEQ ID NO: 3) and 5'-GTACA-3' (SEQ ID NO: 4) sequences, or so-called "sticky-ends"). After annealing is complete, the ends of the hairpin oligonucleotides are ligated, either by chemical or enzymatic means, to provide a larger single-stranded DNA circle in the form of a "dumbbell." Of course, the sizes of the starting hairpin oligonucleotides can be pre-determined, as can be the sequences of the circles. Following ligation, the "dumbbell" shaped product is heat denatured to yield a single-stranded circular product which, due to the circular shape, does not re-anneal.

The present invention is directed to a simple and rapid method of synthesizing single-stranded DNA circles of varying size and sequence. The method disclosed according to the present invention makes use of the tendency of complementary DNA sequences to anneal to each other whether present as part of a larger single DNA sequence or when present on different polynucleotides.

Current technology prepares pre-formed circles for rolling circle amplification (RCA) by ligation of a chemically synthesized oligonucleotide. For ligation, the respective 5'- and 3'-ends are brought together using a short guide oligonucleotide. Unligated linear DNA and the guide oligonucleotides are then digested with a combination of exonucleases. The entire process involves several steps that operate with varying efficiency. Additionally, the yield of circular monomers (i.e., single-stranded DNA circles) can be severely limited by competing reactions (e.g., linear and circular concatamer formation). Thus, some form of optimization is commonly required to improve yield of the monomeric circles. One often used solution is to perform the ligation step at low oligonucleotide concentration. However, this has proven useful only in small scale preparations and has been found unpractical and uneconomical for larger scale, such as commercial, preparations. Other approaches to generate longer circles (e.g., RCA itself and asymmetric PCR) also require a ligation step.

The methods disclosed herein according to the present invention rely on a more straightforward, though novel, approach. The present invention makes use of the well-known coherent end (or "sticky end") method of joining DNA segments. Briefly, each oligonucleotide is designed to form a short hairpin, or linear duplex segment, followed by an overhang such that the overhang on one hairpin oligonucleotide is complementary to the overhang on another hairpin oligonucleotide thereby resulting in a double hairpin dimer ready for closure by ligation by either enzymatic or chemical means.

In accordance with the present invention, there are provided predetermined hairpin oligonucleotide sequences containing short stretches of complementary sequences, perhaps as few as 5 or 6 nucleotides, such that these complementary stretches will anneal to provide a hairpin oligonucleotide. As used herein, the term "hairpin oligonucleotide" refers to a single stranded polynucleotide containing complementary sequences at or near each of its 5'- and 3'-ends such that said complementary sequences anneal, resulting in the formation of a circular structure held in the circularized form by the hydrogen bonded internally complementary sequences. The difference between hairpin oligonucleotides and actual single-stranded DNA circles, such as those formed by the methods disclosed herein, is that the single-stranded circles are held together by covalent bonds to form single circles with no internal hybridization and without free 5'- and 3'-ends. In addition, the starting hairpin oligonucleotides disclosed herein contain internal complementary sequences that are inverted relative to each other so that the 3'- and 5'-ends, where said sequences are located, will hybridize within the same segment to yield a short linear segment with only the non-hybridized portion of the polynucleotide forming a circular structure. In addition, only one of said complementary sequences will be located at either the 5'- or 3'-end of the polynucleotide with the other complementary sequence being displaced from the end of said polynucleotide by a short segment of nucleotides that is not complementary to any portion of the polynucleotide of which it is a part.

A hairpin oligonucleotide that is useful in the methods of the invention comprises a single-stranded oligonucleotide having a short double-stranded portion formed of two self-complementary segments having a loop at one end and a short overhanging single strand at the other so that the ends of said double-stranded portion are not blunt. Thus, for purposes of the present invention, a hairpin may be defined as a double-helical region formed by base-pairing between adjacent, inverted complementary sequences in a single-stranded DNA, preferably within the same single stranded DNA.

Thus, the present invention is directed to a process for preparing multiple copies of single-stranded circular DNA, comprising contacting 2 or more hairpin oligonucleotides, wherein each hairpin oligonucleotide contains at least one segment that does not hybridize with any segment of the same or another of said hairpin oligonucleotides, and wherein each said hairpin oligonucleotide contains a complementary terminal sequence, under conditions permitting said complementary terminal sequences to hybridize, and then ligating the resulting hybridized hairpin oligonucleotides to form single-stranded dumbbell-shaped DNA monomers (such structure is essentially a monomer comprising a double-stranded linear segment with a loop at each end). Following ligation, the single-stranded dumbbell shaped product is heat denatured by means well known in the art to form a fully open single-stranded DNA circle which, despite the presence of the complementary sequences within the circle, will now no longer anneal and thus will remain a single-stranded circle. Appropriate denaturation conditions commonly require temperatures in the range of 70° C. to as much as 100° C., with temperatures of about 95° C., or at least 95° C., being sufficient for most DNA circles.

In one embodiment of the present invention, two 100-mer (i.e., 100 base) oligonucleotides, each with a 5 base pair hairpin and a 4 nucleotide overhang, were used to prepare a 200 nucleotide single-stranded circle. In general, the longer the oligonucleotide the longer the hairpin needed to prepare a stable hairpin-loop that can be ligated. Conversely, present chemical technology does not readily facilitate the preparation of single-stranded circular oligonucleotides of longer than about 100 bases in length. Thus, efficiency in chemically synthesizing long single-stranded oligonucleotides, for example, any circles larger than about 70 nucleotides in length, is very low.

In accordance with one embodiment of the present invention, there is provided a first hairpin oligonucleotide of single-stranded DNA having a general structural arrangement as follows:

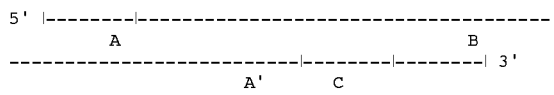

Here, A, B, A', and C represent individual segments of nucleotides within a larger polynucleotide such that segments A and A' are complementary to each other in the usual sense, or Watson-Crick sense, with adenine bases hydrogen bonding to thymine bases and guanine bases hydrogen bonding to cytosine bases. However, segments A and A' are complementary only when segment A is read in the 5' to 3' direction and segment A' is read in the 3' to 5' direction. The result of hybridization of segments A and A' is the formation of a hairpin oligonucleotide with a short stretch of linear duplex DNA at one side of the hairpin oligonucleotide with single stranded segment C extending outward from the short linear duplex and away from the rest of the circle. The resulting structure is depicted in FIG. 1.

A specific embodiment of the hairpin oligonucleotide disclosed according to the present invention may therefore have the following structure:

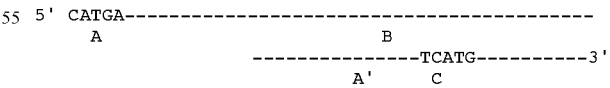

Here, segment A has the sequence 5'-CATGA-3' (SEQ ID NO: 5) and segment A' has the sequence 5'-TCATG-3' (SEQ ID NO: 6). Segment C is a tail segment that has a sequence pre-selected so as to be different from the sequences complementary to either segments A or A', or even from segment B, thereby preventing any complementarity with those sequences and thus preventing unwanted internal annealing. Segment B is a segment having a pre-determined nucleotide sequence which sequence is to be incorporated into the single-stranded circular DNA formed by operation of the invention disclosed herein. Thus, the sequence of segment B is determined by the desires, inclinations and motivations of the user of the present invention, based on the single-stranded DNA circles one desires to synthesize.

Also in accordance with this embodiment of the present invention there is provided a second single-stranded DNA hairpin oligonucleotide having the same general structure as the aforementioned first single-stranded DNA hairpin oligonucleotide. In general, the sequences of the individual segments of the second hairpin oligonucleotide will be different from, and unrelated to, the sequences of the segments of the first hairpin oligonucleotide, with the exception of segment C. The sequence of segment C of the first hairpin oligonucleotide and the sequence of segment C of the second hairpin oligonucleotide are complementary to each other but only when read in opposite directions. For example, if the sequence of segment C of hairpin oligonucleotide 1 has the sequence: 5'-TGTAC-3' (SEQ ID NO: 3) then the sequence of segment C of hairpin oligonucleotide 2 will have the sequence: 5'-GTACA-3' (SEQ ID NO: 4).

In practicing the methods of the present invention it is unnecessary for segment C of each of the hairpin oligonucleotides to be at the 3'-end of the hairpin oligonucleotide but, instead, each segment C could occur at the 5'-end of each of the hairpin oligonucleotides with no effect on the success of the methods disclosed herein. The only requirement is that these segments be complementary when read in opposite directions and that they both occur at either the 3' ends of the hairpin oligonucleotides or at the 5'-ends of the hairpin oligonucleotides but, for the present invention to operate, the respective segments C must not occur at the 5'-end of the first hairpin oligonucleotide and at the 3'-end of the second hairpin oligonucleotide, or vice versa.

In accordance with the present invention, segment B of each hairpin oligonucleotide will comprise, or a portion of such segment will commonly comprise, a pre-determined nucleotide sequence to be incorporated into a single-stranded DNA circle. Said pre-determined sequence will have a nucleotide sequence dictated by the needs and desires of the user of the methods disclosed herein. Such pre-determined sequence may be a sequence derived from a naturally occurring polynucleotide, such as from a plasmid or the genome of an organism, or may be a wholly novel sequence, including a novel sequence synthesized de novo expressly for incorporation into single-stranded circles.

In keeping with one embodiment of the present invention, segment B of each of the first and second starting hairpin oligonucleotides may have the same nucleotide sequence, or similar sequences, but the sequences of these segments will commonly differ. Thus, a reaction mixture may contain one or more copies, commonly many copies, of a first hairpin oligonucleotide containing a segment B having a pre-determined nucleotide sequence, and one or more copies, commonly many copies, of a second hairpin oligonucleotide containing a segment B having the same or, commonly, a different, nucleotide sequence.

In one embodiment of the present invention, a reaction medium will contain a mixture of hairpin oligonucleotides comprised of at least two types. The first type, or population, of hairpin oligonucleotides will have the general structure already described, with a pre-determined sequence, located in segment B, that may or may not be a sequence of interest to the user. The second type, or population, of hairpin oligonucleotides will contain a segment B having a pre-determined sequence whose incorporation into single-stranded circles is desired. Further, the first and second populations of hairpin oligonucleotides will be so structured that their overhang sequences (designated segment C herein) will be complementary and will hybridize upon mixing of the two populations of hairpin oligonucleotides. Thus, segment C in any hairpin oligonucleotide from population 1 will be the same but different from the sequence of segment C from any of the hairpin oligonucleotides of population 2, and vice versa.

In a further embodiment of the present invention, a reaction medium will contain 3 or more populations of hairpin oligonucleotides, one of which will contain a segment B with a pre-determined nucleotide sequence that may, but need not, be essential to the nature of the single-stranded circular products to be formed. Conversely, the other populations of hairpin oligonucleotides will differ solely in the sequence of segment B as described herein. In one such embodiment, there may be 3 such populations wherein each will differ in the sequence of its respective segment B. In this case, hairpin oligonucleotides of population 1 will all have the same sequence for segment C whereas populations 2 and 3 will all have the same sequence for segment C but this sequence will be complementary to that of segment C of population 1. Thus, upon mixing the 3 populations, hairpin oligonucleotides of population 1 will hybridize through segment C with the corresponding complementary segment C of the hairpin oligonucleotides of populations 2 and 3 to form 2 distinct populations of single stranded DNA circles, each product circle being formed from a hairpin oligonucleotide from population 1 and 2 or from population 1 and 3. Because of the identity of the sequence of segment C, hairpin oligonucleotides of population 1 cannot hybridize to other hairpin oligonucleotides of population 1. Because hairpin oligonucleotides of populations 2 and 3 have the same sequence for their own segments C, hairpin oligonucleotides from populations 2 and 3 cannot hybridize to each other but only with hairpin oligonucleotides of population 1.

In keeping with the method of the present invention, another embodiment can have 4 populations of hairpin oligonucleotides. In this case, a reaction mixture would contain, for example, many copies of hairpin oligonucleotides of population 1, containing unique DNA sequences for segments B and C. Conversely, populations 2, 3, and 4 will each contain hairpin oligonucleotides with unique sequences for their respective segments B but each will have the same sequence for their respective segments C, which sequence will be complementary to the sequence of segment C of the hairpin oligonucleotides of population 1.

By continuing with this process, all manner of combinations and permutations of the hairpin oligonucleotides disclosed according to the present invention can be used to form any desired number of unique single-stranded DNA circles.

In accordance with the present invention, the starting populations of hairpin oligonucleotides need not only differ in sequence but, of course, in size and relative concentration. Thus, for example, in the case of 5 populations of hairpin oligonucleotides, population 1 will be of whatever sequence and size is dictated by the needs, inclinations and motivations of the researcher, or other user, while populations 2, 3, 4, and 5 will likewise contain sequences, and be of whatever sizes, the researcher, or other user, desires. Further, the individual concentrations of populations 2, 3, 4, and 5 will likewise be those dictated by the exigencies of the experiments, or other procedures, requiring the synthesis of single-stranded DNA circles. Of course, the relative concentrations of the unique single-stranded DNA circular products will correspond to the relative concentrations of the unique starting hairpin oligonucleotides. In carrying out the methods disclosed herein, it will thus be essential to insure sufficient amounts of hairpin oligonucleotides of population 1 so as to secure complete reaction of the hairpin oligonucleotides of the other populations. Thus, hairpin oligonucleotides of population 1 can be essentially a kind of "universal" hairpin oligonucleotide available merely for forming a circle with other hairpin oligonucleotides whose sequences and sizes are more essential to the nature of the single-stranded DNA circles whose production is desired.

Thus, according to the method disclosed herein, the populations of hairpin oligonucleotides will differ mainly in the nucleotide sequence of their respective segments B. Thus, each pre-selected segment B, or pre-selected sequence forming a portion of segment B, may be the same or different. If all such sequences are the same, then the result of applying the method of the present invention will be to generate many copies of the same sequence with each round and give rise to multiple copies of identical single-stranded DNA circles. Alternatively, if the pre-selected sequences forming, or which are part of, segment B within the hairpin oligonucleotides of the different populations are different in sequence and/or size, the result of applying the method of the present invention will be to generate equimolar quantities of multiple copies of single-stranded DNA circles containing each of the pre-selected sequences with the circles corresponding to each of the selected segments being of either the same size but different in sequence, or different in both size and sequence. The number and nature of the products produced by the method of the present invention are therefore limited only by the desires and motivations of the user.

The hairpin oligonucleotides used as starting materials in the methods of the present invention may be prepared synthetically, using either automation or conventional chemistry, for example by attaching a starting structure to beads and adding nucleotides thereto. The hairpin oligonucleotides for use in the present invention may also be prepared by synthesizing segments or fragments thereof and then joining said segments or fragments into larger structures containing appropriate nucleotide sequences for use herein. Such segments or fragments may also be of natural origin, deriving from microorganisms in nature or the result of cloning of sequences within selected organisms and utilizing selected vectors for the cloning process. Such segments or fragments may also derive from natural vectors, such as plasmids, viruses, or the like.

The hairpin oligonucleotides for use in the present invention may also be hybrids, or chimeras, containing some segments or sequences that are of natural origin as well as segments or sequences wholly synthetic in origin. Of course, the fact that a given segment or sequence is found in nature does not prevent it from being prepared synthetically in the laboratory for use herein. Thus, the sources available for the hairpin oligonucleotides, or fragments, or segments, or portions thereof, for use in the present invention are left to the skill and imagination of the researcher, or other user of the present invention.

As used herein, the terms "portion," "segment," and "fragment," when used in relation to polynucleotides or oligonucleotides of any kind, including the hairpin oligonucleotides described herein, refer to a continuous sequence of nucleotide residues, which sequence forms a subset of a larger sequence. For example, if a polynucleotide were subjected to treatment with any of the common endonucleases, the oligonucleotides resulting from such treatment would represent portions, segments or fragments of the starting polynucleotide(s).

Following hybridization of the complementary, or cohesive, ends of hairpin oligonucleotides to form pairs like those depicted in FIG. 1, the sequences of the respective hybridized hairpin oligonucleotides are then closed using any of several forms of DNA ligation. Such ligation can involve a reaction catalyzed by an enzyme, including any of several well known, and often used, DNA ligases, such as T4 ligase or *E. coli* ligase, or Ampligase, or can involve no enzymes and, instead, comprise a simple chemical reaction, such as that used in DNA synthetic procedures, for example, reactions involving phosphorothioate derivatives or other reactive groups. The latter, of course, may prove more cumbersome than a simple enzyme reaction.

For ligation employing an enzyme-catalyzed reaction, a general procedure can involve combining 50 pmol (1 pmol=1 picomole or $10^{-12}$ moles) of one prepared population of hairpin oligonucleotides with 50 pmol of a second population, or any number of populations such that the total amount of DNA is about 100 pmol. The hairpin oligonucleotides are at this time suspended in ligase buffer (50 mM Tris-Cl, 1 mM $MgCl_2$, and 1 mM dithiothreitol, 0.1 mM ATP, pH 7.6) at 0° C. until addition of ligase. Hybridization of the hairpin oligonucleotides can, of course, be allowed to occur during the ligation reaction so that the enzyme ligates the cohesive, or sticky, ends as hybridization proceeds. A preferred DNA ligase is that of phage T4, which requires ATP (adenosine triphosphate) for its reaction (already contained in the above-recited ligase buffer). If *E. coli* ligase is used instead, $NAD^+$ (nicotinimide adenine dinucleotide) must be used in place of ATP. If reaction volume is a total of 10 μL, then the ligase reaction commences with the addition of 3 Weiss units of T4 DNA ligase, incubated at about 37° C. for about 3 hours, a time period that will vary with cohesive ends and with other parameters so that this must be optimized by the researcher to obtain the best results. In any event, incubation temperatures will generally be between 4° C. and about 65° C. Optionally, the buffers can be prepared at higher concentration and then diluted with a suitable amount of water.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

In addition to ligation using enzymes, chemical methods are also available for use with the present invention. These include, for example, the formation of phosphorothioate derivatives of terminal nucleotide residues and subsequent ligation. Such methods are well known in the literature, being commonly used for nucleotide synthesis. [See: U.S. Pat. No. 5,859,232 and U.S. Pat. No. 5,151,510 (and references contained therein) for synthetic procedures]

Consequently, the method disclosed according to the present invention allows single-step generation of various sized circles of DNA having uniquely known (i.e., either pre-determined or pre-selected) sequences. The synthesis of such a product is therefore ideal for producing preformed circles for multiplexing RCA (rolling circle amplification). Also, because the sequences of the starting DNA are known, it is a straightforward matter to produce primers and probes specific for each of the circles. Further, circles are produced at the outset and not linear sequences of DNA that must still be ligated before proceeding further. In accordance with the present invention, enzymatic ligation can proceed at the same time, and in the same reaction mixture, as the initial hybridization step.

The circles made by the invention are frequently used for signal amplification by RCA. For example, a target DNA/RNA sequence is recognized by a bifunctional oligonucleotide which also serves as a primer for RCA using a circle made by the invention. Since many different circles are made simultaneously it is possible to detect multiple targets in a single sample at once. Many other and different uses for the single-stranded circles produced according to the methods of the invention are described in the Ruth and Driver reference cited above (WO 92/01813).

In accordance with the present invention, targets are detected by rolling circle amplification (or RCA). Such targets can be any molecules that can be detected using RCA methods, including DNA, RNA and proteins. Thus, for example, proteins can be employed by using an antibody conjugated to an oligonucleotide. DNA/RNA targets can be employed using bifunctional oligonucleotides. One arm of the bifunctional oligonucleotide recognizes and anneals to the target whereas the other arm acts as a primer for RCA. Thus, any molecule that can be tagged with an oligonucleotide can then be detected by RCA methodology using circles made according to the present invention.

The single-stranded DNA circles made according to the invention find a variety of other uses. In particular, they are substrates for further rolling circle amplification. In one such embodiment, a target DNA or RNA sequence present in a biological sample is recognized by a bifunctional oligonucleotide, which oligonucleotide then serves as a primer for rolling circle amplification using the single stranded circles made according to the invention as template. Since many different circles can be made, the methods of the invention facilitate the detection of multiple targets in a single sample (referred to as multiplexing). In this way, the relative concentration of targets in a biological sample can be detected since such molecules will serve to replicate the different single-stranded circles in proportion to the level of target in the test sample, the latter process being carried out by conventional rolling circle amplification. Such conventional rolling circle amplification can be effected by a variety of commonly available enzymes, including *E. coli* DNA polymerase I, Klenow fragment, T4 or T7 DNA polymerases, Taq polymerase, and others.

Figure 2:
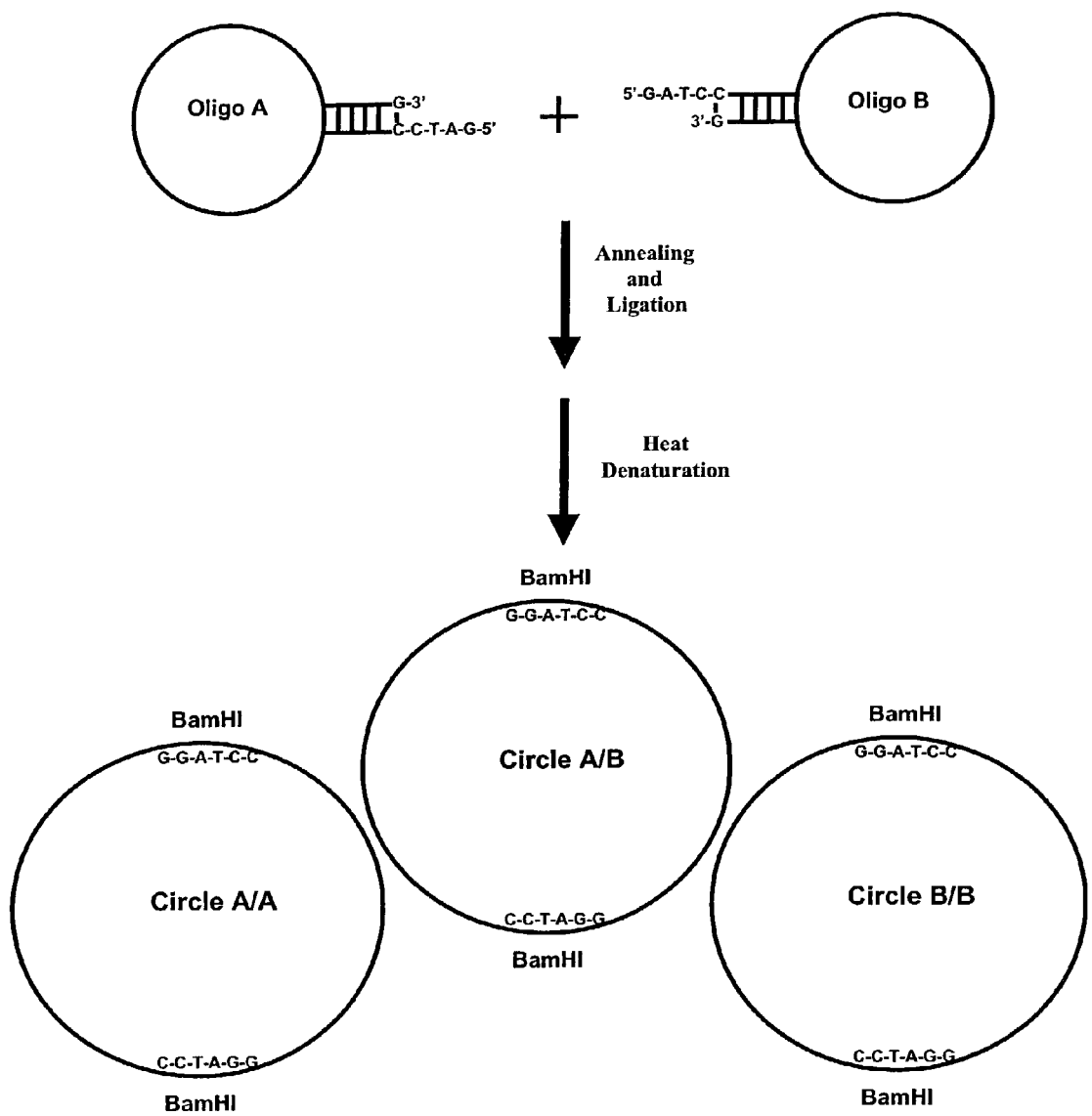
FIG. 2 shows an example of hairpin oligonucleotide ligation wherein the resulting duplex sequence forms a BamHI restriction nuclease site, with subsequent formation of a single-stranded circle.
Figure 3:
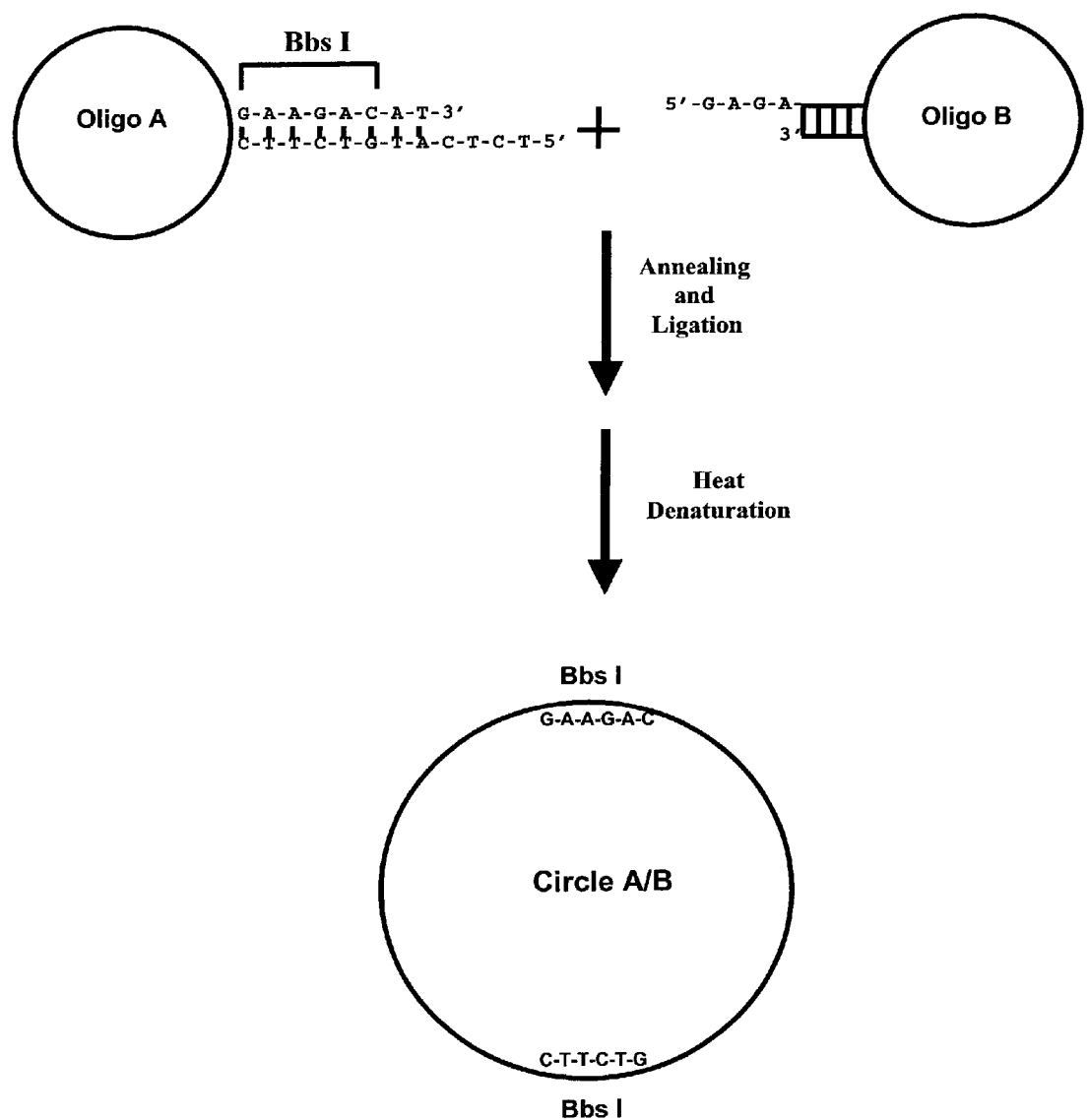
FIG. 3 shows an example of hairpin oligonucleotides that, on ligation, form non-palindromic restriction nuclease sites, here Bbs I, and eventually forming a single-stranded DNA circle using the method disclosed herein.

Also in accordance with the present invention, the double-stranded linear segment formed from the ligation of the hairpin oligonucleotides comprises at least one substrate sequence for at least one restriction endonuclease (see FIGS. 2 and 3 for specific examples).

Also in accordance with the present invention, the mixture of hairpin oligonucleotides can also comprise a non-circular DNA duplex segment, formed by direct chemical synthesis or by the action of one or more restriction nucleases on a larger circular or non-circular DNA structure and wherein said non-circular, or linear, duplex DNA segment contains at least one linear terminal sequence complementary to at least one hairpin oligonucleotide complementary terminal sequence and wherein following ligation the resulting double-stranded linear segment of the aforementioned dumbbell shaped product contains said non-circular duplex DNA between said two circular portions.

In a preferred embodiment, a non-circular DNA duplex segment has a linear terminal sequence at each end wherein each said terminal sequence is complementary to a hairpin oligonucleotide complementary terminal sequence.

In accordance with the present invention, hybridization of a hairpin oligonucleotide with a linear terminal sequence of the non-circular DNA duplex forms, or completes formation of, a restriction nuclease substrate sequence. Thus, in a preferred embodiment the double-stranded linear segment resulting from ligation of said non-circular DNA duplex segment and hairpin oligonucleotides comprises a restriction nuclease substrate sequence.

In another preferred embodiment, the double-stranded linear segment resulting from ligation of said non-circular DNA duplex segment and hairpin oligonucleotides comprises two restriction nuclease substrate sequences.

In one embodiment, hairpin oligonucleotides can be ligated to the ends of DNA restriction fragments of any desired size and sequence identity and then used to prepare circles. In a preferred embodiment, a segment of DNA is cut using a known restriction enzyme and the coherent ends used for ligation to a hairpin oligonucleotide (See FIG. 4). To avoid self-ligation, two different restriction nucleases can be used, each producing a different but known coherent end. Following the heat denaturation step of the present invention, a circle is formed. In one highly preferred embodiment, this method is used to amplify unknown sequences by RCA since the ligated hairpin oligo can be utilized for RCA priming. The only sequence information required for such a procedure is the identity of the overhangs of the restriction fragment (which are always known since these are defined by the user in choosing the restriction nucleases used to form them). Such methods can be readily used to amplify unknown genomic DNA, viral DNA, as well as cDNA libraries. RCA amplified DNA can then be used directly for sequencing or it can be cloned. In fact, the starting fragment and oligonucleotide could even be regenerated after amplification by digesting the RCA product with the original restriction enzyme(s).

Advantages of such a procedure include the fact that the sequences are replicated in proportion to their occurrence in the substrate mixture, detection of target sequences is independent of the structure of the sequence, and further that the detection of the relative amounts of multiple molecules of interest is facilitated.

Of course, for use in the methods disclosed and claimed herein, it is unnecessary for the linear segment of DNA to be produced by restriction nuclease, since direct chemical synthesis thereof is a completely suitable option for producing such segments. For example, in FIG. 4, the non-circular duplex DNA, or linear segment composed of at least partially complementary strands C and W, can be generated by application of one or more restriction nucleases to a larger segment, circular or non-circular, of DNA to form said non-circular, or linear, duplex DNA. In addition, said non-circular, duplex DNA can be formed by direct chemical synthesis to form said duplex segment. Further, for use in the methods of the present invention, such non-circular duplex DNA need not necessarily incorporate any restriction nuclease sites or may optionally incorporate a restriction nuclease site other than at the ends of such non-circular duplex DNA segment, such as in the middle of such segment and wherein such structure may or may not contain one or more such sites at or near the ends of such segment.

Figure 4:
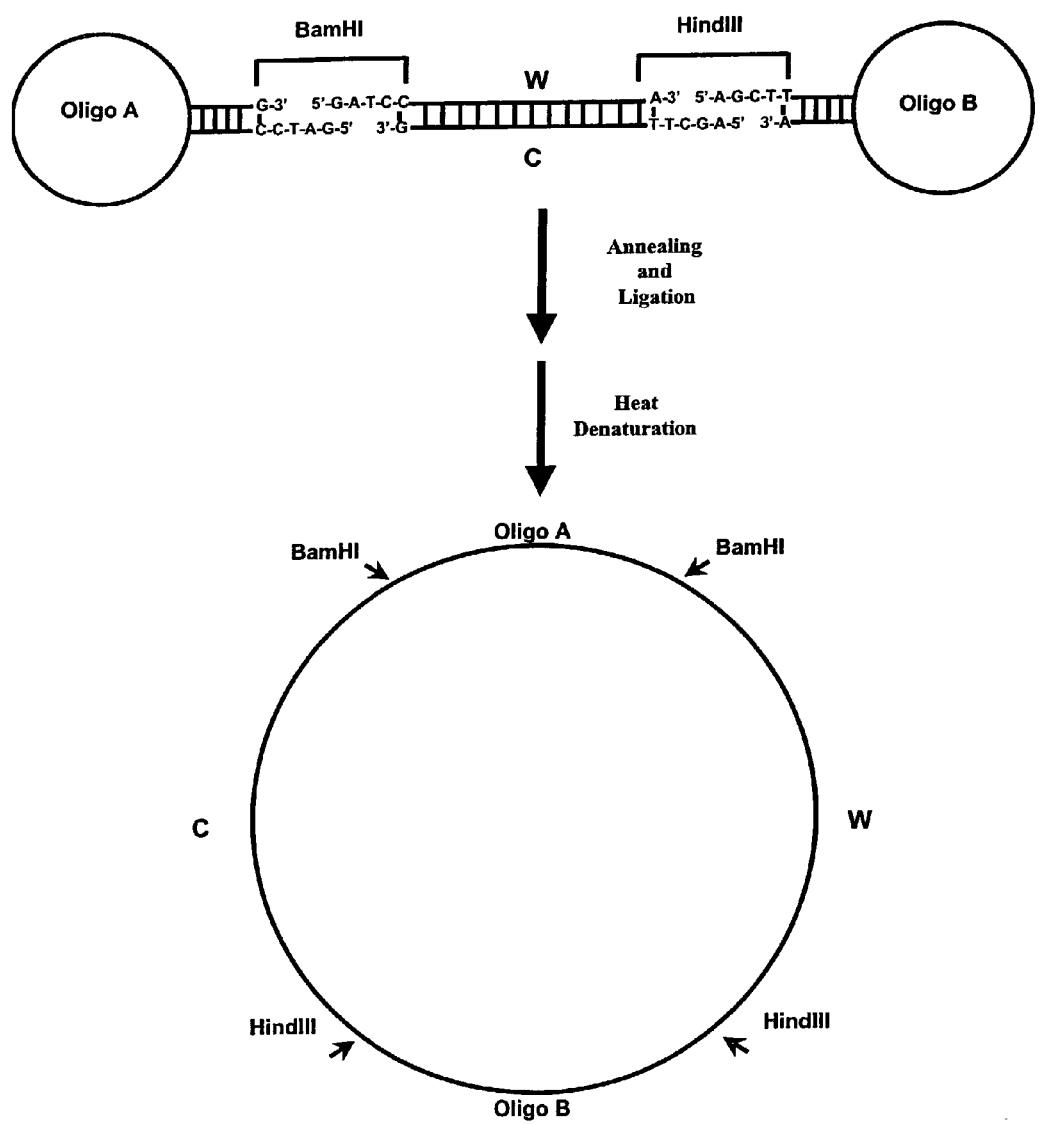
FIG. 4 shows an example of ligation of hairpin oligonucleotides to a restriction enzyme fragment, or non-circular duplex DNA with strands W and C and having a single-stranded overhang at each end such that after hybridization with hairpin oligonucleotides, and subsequent ligation, the linear duplex sequences formed thereby represent restriction sites, which sites will be singular following eventual formation of a single-stranded DNA circle following annealing, ligation and heat denaturation. Such sites can then be duplexed at a later stage by hybridization with selected target sequences and used for selective attack by the corresponding restriction nuclease(s). After amplification by rolling circle amplification (RCA) such sites can be duplexed by self-annealing and then cut by the corresponding restriction nuclease(s) to regenerate the original or starting restriction enzyme fragment.

Furthermore, the non-circular duplex DNA segments, such as is disclosed in FIG. 4, as one example, may have single-stranded overhangs at one or both ends and having selected sequences such that, when hybridized to the overhangs of other DNA segments, either other non-circular duplex DNA segments and/or hairpin oligonucleotides, will form duplex restriction nuclease sites following ligation thereof in accordance with the methods disclosed herein. It should be borne in mind that, while interaction of two hairpin oligonucleotides and a single non-circular duplex DNA segment is depicted in FIG. 4, other and different combinations will no doubt suggest themselves to those of skill in the art yet still fall within the bounds contemplated by the present invention.

While avoiding numerous disadvantages, the method of the present invention affords numerous advantages in the preparation of single-stranded circular DNAs. First, it represents a method to directly generate circles, since all current methods involve ligation (either by chemical or enzymatic means) of linear oligonucleotides. Thus, current methodology is highly inefficient and requires the use of a battery of other enzymes or chemical steps. Conversely, with the methodology disclosed herein, such circles are generated immediately and directly from a predetermined reactant with no need for further processing or enzymatic treatments. In addition, the method of the present invention affords the only means of simultaneously generating any desired number of different (in size or sequence) circles, for multiplexing and other uses, and with no size limitations on the products to be formed. For example, using the methods disclosed herein it is a simple matter to prepare single-stranded DNA circles of sizes anywhere from 50 bases to greater than 5,000 bases, and any manner of combinations in between.

In one embodiment of the present invention, there are provided hairpin oligonucleotides with complementary ends (i.e., complementary overhang regions) that comprise restriction sites for endonucleases to provide, after appropriate ligating and denaturing, single stranded circles whose RCA products can be cut by the same restriction enzyme to regenerate hairpin oligonucleotides, thereby providing, inter alia, an enzymatic source of oligonucleotides for production of circles without the need of chemical synthesis (see FIGS. 2 and 3). As opposed to the situation with hairpin oligonucleotides having phosphorothioate derivatives protecting the restriction site, the present invention provides an enzymatic factory for simultaneous RCA, cutting and ligating.

In utilizing the methods disclosed herein, all the circles will share one pair of common short sequences that combine the remnants of the terminal sequence complementary and the complementary sequence forming the hairpin region, now separated from each other in the larger circle (see FIG. 1), which can then be used for priming (for example, for RCA, or rolling circle amplification, or sequencing) using a primer complementary to one of the sequences, or a pair of complementary primers each complementary to one or the other of the sequences present in the single stranded circles.

The present invention also relates to a kit containing a sample of the aforementioned neutral or reference hairpin oligonucleotides having a defined nucleotide sequence and containing a specified terminal sequence for hybridization and ligation to hairpin oligonucleotides of pre-determined sequence and useful for forming single-stranded DNA circles. The hairpin oligonucleotides of pre-determined sequence can then be designed so as to have segment C regions with sequences complementary to the specified segment C sequences of the neutral or reference hairpin oligonucleotides. Such a kit may optionally contain a sample of T4 ligase for use in carrying out the ligation part of the methods disclosed herein. Such kit may also optionally contain a sample of ligase buffer, as disclosed herein, said buffer being present in powdered form, possibly in a concentrated state, and ready for immediate reconstitution with water. Where said buffer powder is present in a concentrated form, this may preferably be a form containing sufficient buffer salt components so that, when reconstituted with water, the resulting buffer concentration will be higher, perhaps 10 fold higher, than the concentration of said buffer components in the final reaction mixture. Such concentrated form of the buffer can thereby serve as a reservoir for adjusting the pH of said buffer solution concentrate, which concentrated solution merely awaits dilution with water to form the actual reaction mixture. In one embodiment, the method disclosed herein would be carried out by adding the appropriate amounts of the hairpin oligonucleotides to a microfuge tube, or other suitable container, adding the required number of units of ligase, suspending in 1 µL of ice cold buffer concentrate and then commencing reaction by addition of the appropriate volume of distilled water at or near the desired reaction temperature so as to achieve a total volume of the aforementioned 10 µL (or whatever volume is proportionately appropriate to the amounts of DNA and ligase the researcher requires).

In a further embodiment of the present invention, the neutral or reference hairpin oligonucleotide may itself be designed so as to contain specific reference, or marker, sequences of nucleotides that are subsequently incorporated into the resulting single-stranded DNA circles and can serve as marker sequences for said circles, available for a variety of uses such as providing a binding site for a universal primer sequence useful in subsequent rolling circle amplification of the single-stranded DNA circles. Thus, all of the resulting single-stranded DNA circles would be amenable to replication (i.e., amplification) using the same primer sequence (a sample of such primer may optionally be supplied with the kit). This would avoid the need for the user of the present invention to incorporate a primer target sequence in each of the preformed hairpin oligonucleotides containing the pre-selected sequences of segment B. Such primer target sequence would be incorporated into the single-stranded DNA circles via the neutral or reference or universal hairpin oligonucleotides common to the reaction with the "user-defined" hairpin oligonucleotide(s) containing the pre-selected sequence(s) of segment B.

In some cases it may be desirable to utilize more than one kind of "user-defined" hairpin oligonucleotide, such as for eventual multiplexing using the resulting single-stranded DNA circles. In such case, it would be important that the relative concentrations of the resulting single-stranded DNA circle populations reflect the relative concentrations of the starting user-defined hairpin oligonucleotides (and their contained pre-selected sequences of interest in their respective B segments). Because of the excess of neutral or reference or universal hairpin oligonucleotides, some of the latter will remain unreacted. To avoid any interference by this population of unreacted hairpin oligonucleotides, the present method, by providing circular products larger than these unreacted components, facilitates ready size separation to yield only reacted circles in direct proportion to the relative concentrations of the starting user-defined hairpin oligonucleotides.

A specific embodiment of the method of the present invention is described in the following non-limiting example. In following the procedure disclosed in the example it is to be clearly kept in mind that other and different embodiments of the methods disclosed according to the present invention will no doubt suggest themselves to those of skill in the relevant art.

EXAMPLE

Oligonucleotide 1 (50 n)-
5'-TGAGCTGTAACTTGTCTCGTATTAAACTAAAGCTGA SEQ ID NO:1
GATCTCACGTACA Oligonucleotide 2 (45 n)-
5'-ACTCAATATAGTTCTTGGAGAAGGTGGAATCACACT SEQ ID NO:2
GAGTTGTAC Oligonucleotides 1 and 2 were mixed at 5 µM each in a 1 ml reaction mixture containing 50 mM Tris-HCl (pH 7.5), 10 mM $MgCl_2$, 10 mM dithiothreitol (DTT), 1 mM adenosine triphosphate (ATP) and 25 µg/ml bovine serum albumin (BSA). The mixture was heated to 65° C. for 5 minutes and allowed to cool at room temperature (24° C.) for 30 minutes. Ligation was initiated by adding T4 DNA ligase to a final concentration of 2,000 ligation units per ml (approximately 30 Weiss units). The ligation mixture was incubated in a water bath for 2 hours at 37° C. Ligation products were analyzed and quantitated by denaturing polyacrylamide gel electrophoresis.

To purify circles, 2,000 units of Exonuclease III were added to reaction mixture and incubation continued for 2 hours at 37° C. The mixture was then heated at 95° C. for 5 minutes to inactivate T4 DNA ligase and Exonuclease III and melt any remaining hairpins present in the unligated, linear oligonucleotides. To complete digestion of linear oligonucleotide the reaction mixture was adjusted by adding 66 µl of 1 M glycine-NaOH buffer (pH 9.5) and 8 µl of 1 M DTT and 55 units of Exonuclease V were added. The reaction was incubated at 37° C. for at least one hour and was then deproteinized by digestion with 50 µg/ml Proteinase K for one hour at 37° C. followed by extraction with 1 ml of phenol:chloroform:isoamylalcohol (25:24:1). The circle DNA was then precipitated by adding 0.5 ml of 7.5 M ammonium acetate and 3.75 ml of 100% ethanol and incubation at −20° C. overnight. The circle DNA was collected by centrifugation in a microfuge at maximum speed for 20 minutes at 4° C. The DNA pellet was rinsed once with 70% ice-cold ethanol and dried under vacuum. Circle DNA was finally resuspended in 10 mM Tris-HCl (pH 7.5), 1 mM EDTA to a concentration of 1–5 µM. The circle DNA was heat denatured to full single stranded form by incubating at 100° C. for 5 minutes followed by quick cooling to 4° C. in a water/ice bath.

---

What is claimed is:

1. A method for simultaneous synthesis of multiple copies of different single-stranded circular DNA molecules, comprising:
   (a) contacting a plurality of universal hairpin oligonucleotides with at least two different target hairpin oligonucleotides, wherein each said hairpin oligonucleotide contains a segment that does not hybridize with any segment of the same or another of said hairpin oligonucleotides and wherein each of said hairpin oligonucleotides comprises a single stranded terminal non-palindromic sequence (segment C) such that said segment C of each universal hairpin oligonucleotide is complementary to the segment C of each target hairpin oligonucleotide but said segment C of any target oligonucleotide is not complementary to segment C of the same or another target hairpin oligonucleotide, and wherein said contacting occurs under conditions promoting said contacting and promoting hybridization of said segments C,
   (b) ligating the resulting hybridized hairpin oligonucleotides to form a population of monomers each comprising a duplex linear segment with a single-stranded loop at each end,
   (c) denaturing said monomers to form single-stranded circles,
   (d) contacting said single stranded circles of step (c) with a plurality of deoxynucleoside triphosphates (dNTPs), multiple primer oligonucleotides comprising at least one oligonucleotide complementary to at least one segment of each of the single stranded circles formed in step (c) and a DNA polymerase capable of supporting rolling circle amplification (RCA), said contacting occurring under conditions promoting said contacting and promoting said rolling circle amplification to form an RCA product,
   thereby simultaneously generating multiple copies of different single-stranded circular DNA molecules.

2. The method of claim 1 wherein the target hairpin oligonucleotides of step (a) are of different sizes.

3. The method of claim 1 wherein at least one of the hairpin oligonucleotides contains a pre-selected nucleotide sequence.

4. The method of claim 1 wherein said duplex linear segment of step (b) comprises at least one endonuclease restriction site.

5. The method of claim 4 further comprising contacting said RCA product of step (d) with an endonuclease specific for said endonuclease restriction site to form a new set of hairpin oligonucleotides and then repeating steps (a) through (c) using said new set of hairpin oligonucleotides.

6. The method of claim 4 wherein the endonuclease restriction site contains a phosphorothioate derivative.

7. The method of claim 1 wherein the ligation step employs an enzyme.

8. The method of claim 7 wherein the enzyme is selected from the group consisting of T4 ligase, Ampligase and *E. coli* ligase.

9. The method of claim 1 further comprising ligation at a temperature of between 4° C. to 65° C.

10. The method of claim 1 wherein the ligation step is non-enzymatic.

11. The process of claim 10 wherein the ligation step requires the formation of a phosphorothioate derivative of a hairpin oligonucleotide.

12. The process of claim 1 wherein said DNA polymerase is a member selected from the group consisting of *E. coli*

DNA polymerase I, Klenow fragment, T4 or T7 DNA polymerases, and Taq polymerase.

13. The process of claim 1 wherein said denaturation is accomplished by heat denaturation.

14. The method of claim 13 wherein the heat denaturation is carried out at a temperature of between 70° C. and 100° C.

15. The method of claim 14 wherein the temperature is at least 95° C.

16. The process of claim 1 wherein said restriction site is a BamHI restriction site and said endonuclease is BamHI.

17. The method of claim 1 wherein said double-stranded linear segment formed in step (b) comprises at least two endonuclease restriction sites.

18. The method of claim 1 wherein said single-stranded circular DNA molecules are produced in a ratio equal to that of the respective starting target hairpin oligonucleotides used to form said circular DNA molecules.

19. The method of claim 1 wherein at least 3 different target hairpin oligonucleotides are contacted with said universal hairpin oligonucleotides.

20. The method of claim 1 wherein at least 4 different target hairpin oligonucleotides are contacted with said universal hairpin oligonucleotides.

* * * * *